(12) United States Patent
Fukuoka et al.

(10) Patent No.: US 7,326,744 B2
(45) Date of Patent: Feb. 5, 2008

(54) LOW DUSTING CRYSTAL TRANSFORMATIONS OF 2,2'-METHYLENEBIS[4-(1,1,3,3-TETRAMETHYLBUTYL)-6-BENZOTRIAZOLYLPHENOL] AND MIXTURE THEREOF, METHOD FOR PREPARING THEM, AND ULTRAVIOLET LIGHT ABSORBER USING THEM

(75) Inventors: Naohiko Fukuoka, Koube (JP); Yoshinori Ohmae, Koube (JP); Yuichi Kaneko, Koube (JP); Masayuki Nishimatsu, Koube (JP)

(73) Assignee: Chempiro Kaei Kaisha, Limited, Koube (JP)

( * ) Notice: Subject to any disclaimer, the term of this patent is extended or adjusted under 35 U.S.C. 154(b) by 0 days.

(21) Appl. No.: 10/493,575

(22) PCT Filed: Jun. 5, 2002

(86) PCT No.: PCT/JP02/05553

§ 371 (c)(1),
(2), (4) Date: Apr. 26, 2004

(87) PCT Pub. No.: WO03/037880

PCT Pub. Date: May 8, 2003

(65) Prior Publication Data
US 2004/0242733 A1 Dec. 2, 2004

(30) Foreign Application Priority Data
Oct. 29, 2001 (JP) .............................. 2001-330582
Mar. 6, 2002 (JP) .............................. 2002-061013

(51) Int. Cl.
C08K 5/3437 (2006.01)
C07D 249/18 (2006.01)

(52) U.S. Cl. .................. 524/91; 548/259; 548/260; 252/401

(58) Field of Classification Search .................. 524/91; 548/259, 260; 252/401
See application file for complete search history.

(56) References Cited

U.S. PATENT DOCUMENTS

| 4,681,905 A | * | 7/1987 | Kubota et al. ................. 524/91 |
| 4,812,498 A | | 3/1989 | Nakahara et al. |
| 4,937,348 A | * | 6/1990 | Kubota ........................ 548/259 |
| 5,229,521 A | | 7/1993 | Luisoli et al. |
| 5,237,071 A | | 8/1993 | Leistner et al. |

FOREIGN PATENT DOCUMENTS

| EP | 0 822 188 A1 | 2/1998 |
| WO | WO 98/46342 A | 10/1998 |

* cited by examiner

Primary Examiner—Kriellion A Sanders
(74) Attorney, Agent, or Firm—Oliff & Berridge PLC

(57) ABSTRACT

The present invention relates to a low dusting crystalline 2,2'-methylenebis[4-(1,1,3,3-tetramethylbutyl)-6-benzotriazolylphenol] type I crystal transformation which exhibits diffraction peaks at diffraction angles (2θ±0.1°) of 7.1°, 8.6°, 14.3°, 16.1°, 18.1° and 23.0° in powder X-ray diffraction analysis with Cu-Kα radiation; a low dusting 2,2'-methylenebis[4-(1,1,3,3-tetramethylbutyl)-6-benzotriazolylphenol] type II crystal transformation which does not exhibit a distinct diffraction peak but an amorphous halo in powder X-ray diffraction analysis with Cu-Kα radiation; a mixture thereof; a method for preparing them; and a UV light absorber, an emulsion composition and a polymer material using them.

18 Claims, 10 Drawing Sheets

LOW DUSTING CRYSTAL TRANSFORMATIONS OF 2,2'-METHYLENEBIS[4-(1,1,3,3-TETRAMETHYLBUTYL)-6-BENZOTRIAZOLYLPHENOL] AND MIXTURE THEREOF, METHOD FOR PREPARING THEM, AND ULTRAVIOLET LIGHT ABSORBER USING THEM

TECHNICAL FIELD

The present invention relates to a low dusting crystalline 2,2'-methylenebis[4-(1,1,3,3-tetramethylbutyl)-6-benzotriazolylphenol] type I crystal transformation which is useful for ultraviolet (UV) light absorbers and a method for preparing the same. In addition, the present invention relates to a low dusting amorphous 2,2'-methylenebis[4-(1,1,3,3-tetramethylbutyl)-6-benzotriazolylphenol] type II crystal transformation which is different from the above-mentioned crystalline transformation, and a method for preparing the same. Further, the present invention relates to mixtures containing these compounds and UV light absorbers using these compounds.

BACKGROUND ART

In recent years, the demand for additives such as flame retardants, antioxidants or UV light absorbers has been increasing with a frequent use of polymer products such as a variety of plastics, synthetic rubbers, nylon fibers or resin coatings. Particularly, in promotion of differentiation of polymer products and making them highly value added, it has become an important problem to use UV light absorbers in order to protect the polymer products against deterioration phenomena due to UV light such as cracks or discoloration, and therefore a stable supply of UV light absorber is required. Representative UV light absorbers include benzophenones, benzotriazoles, cyanoacrylates, salycylates and the like, and they are generally used by kneading into polymer materials as they are, by adding to a coating or an oil, etc. or by preparing an emulsion composition thereof and allowing it to adsorb on fibers. A large number of UV light absorbers known hitherto are excellent in efficiency of UV light absorption, but have problems such as sublimation or volatilization when they are kneaded into polymer materials and heated or processed, or problems that they are gradually volatilized and scattered when the finished products are used. In order to overcome these problems, improvements such as a polymerization of UV light absorbers or an addition of non-volatile functional groups thereto have been attempted, but none was proven to be fully satisfactory. In addition, when UV light absorbers in a polymerized state are handled in a shape of powder, most of them have problems such as dust scattering, low flowability or low shelf stability, and they are required to be improved in powder properties.

It is generally known that 2,2'-methylenebis[4-(1,1,3,3-tetramethylbutyl)-6-benzotriazolylphenol] is effective as UV light absorbers for plastics, coatings, oil, fibers and the like.

The method of preparation of 2,2'-methylenebis[4-(1,1,3,3-tetramethylbutyl)-6-benzotriazolylphenol] is disclosed in Japanese Patent Laid-open No. Sho 61-115073 in which 4-(1,1,3,3-tetramethyl)butyl-6-benzotriazol-2-yl phenol is reacted with a dialkylamine and formalin to give a Mannich base, and a reaction crude product obtained upon treating the resulting Mannich base with a base is crystallized from heptane, in Japanese Patent Laid-open No. Hei 4-29087 in which 4-(1,1,3,3-tetramethyl)butyl-6-benzotriazol-2-yl phenol is reacted with a dialkylamine and formalin to give a Mannich base, and a reaction crude product obtained upon treating the resulting Mannich base with a base is crystallized from xylene, or in Japanese Patent Laid-open No. Hei 5-213908 in which 4-(1,1,3,3-tetramethyl)butyl-6-benzotriazol-2-yl phenol and formalin are reacted with concentrated sulfuric acid to give a reaction crude product and the resulting crude product is crystallized from methanol.

However, these patent publications do not describe powder properties such as scattering, flowability or stability on storage of solid-like substances obtained by the method disclosed therein, nor crystalline state of the solid-like substances. Further, only the use of methanol, xylene or heptane as solvent for crystallization is described in examples of the above-mentioned patent publications.

On the other hand, it is generally known that there occurs problems such as dust scattering, low flowability or concretion on storage when the solid-like substances are handled. In order to solve these problems, various investigations are undertaken on crystalline state of the solid-like substances. For example, Japanese Patent Laid-open Nos. Hei 6-128195 and Hei 6-72960 disclose that there are difference in bulk specific gravity, particle size distribution and flowability of powders in each crystal transformation for the same compound. As mentioned above, it is known that even if two compounds belong to the same compound, they are different from each other in functionality or physical properties depending on in what crystal state they are. It is important to obtain such an information for a tendency in order to heighten the added value of products and an improvement in quality thereof. In addition, as practical methods for analyzing substances from the view point of crystal, X-ray diffraction analysis and differential scanning calorimeter analysis are used in various fields such as differentiation of crystal states or development of new functional materials.

2,2'-methylenebis[4-(1,1,3,3-tetramethylbutyl)-6-benzotriazolylphenol] prepared by the known methods is in a form of fine powder, and causes problems in workability such as scattering or partial agglomerate of the powder during handling including weighing in drying step or packaging step and feeding. Thus, it is desired to provide solid with good flowability which does not affect adversely workability in handling of the powder.

The object of the present invention is to provide a low dusting crystalline 2,2'-methylenebis[4-(1,1,3,3-tetramethylbutyl)-6-benzotriazolylphenol] type I crystal transformation and a low dusting amorphous 2,2'-methylenebis[4-(1,1,3,3-tetramethylbutyl)-6-benzotriazolylphenol] type II crystal transformation which have excellent UV light absorptive power, exert little sublimation or volatilization, are easy to handle and excellent in workability at use, and cause little dust; methods for preparing these compounds, mixtures containing these compounds and UV light absorbers using these compounds.

DISCLOSURE OF INVENTION

1) A first aspect of the present invention relates to a low dusting crystalline 2,2'-methylenebis[4-(1,1,3,3-tetramethylbutyl)-6-benzotriazolylphenol] type I crystal transformation (this crystal transformation is hereinafter referred to also as "type I crystal transformation") of formula (1)

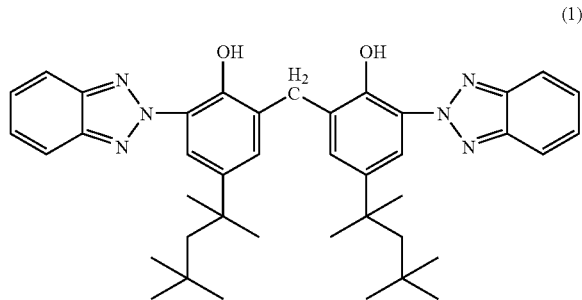

(1)

which exhibits diffraction peaks at diffraction angles (2θ±0.1°) of 7.1°, 8.6°, 14.3°, 16.1°, 18.1° and 23.0° in powder X-ray diffraction analysis with Cu-Kα radiation.

2) A second aspect of the present invention relates to the crystalline 2,2'-methylenebis[4-(1,1,3,3-tetramethylbutyl)-6-benzotriazolylphenol] type I crystal transformation as set forth in the above-mentioned 1), which has a compaction degree of 35 or less in powder test.

3) A third aspect of the present invention relates to a method for preparing the crystalline 2,2'-methylenebis[4-(1,1,3,3-tetramethylbutyl)-6-benzotriazolylphenol] type I crystal transformation as set forth in the above-mentioned 1) or 2), characterized by crystallizing 2,2'-methylenebis[4-(1,1,3,3-tetramethylbutyl)-6-benzotriazolylphenol] in the presence of ketone.

4) A fourth aspect of the present invention relates to 2,2'-methylenebis[4-(1,1,3,3-tetramethylbutyl)-6-benzotriazolylphenol] type II crystal transformation (this crystal transformation is hereinafter referred to also as "type II crystal transformation") of formula (1)

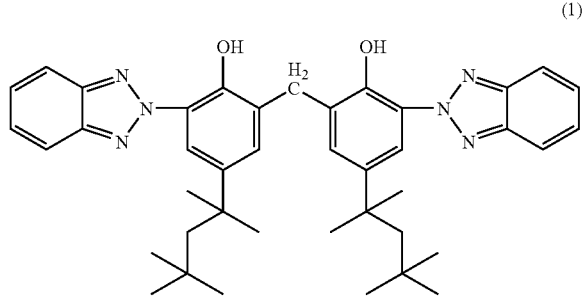

(1)

characterized in that does not exhibit a distinct diffraction peak but a halo in powder X-ray diffraction analysis with Cu-Kα radiation and that is amorphous.

5) A fifth aspect of the present invention relates to a mixture of 2,2'-methylenebis[4-(1,1,3,3-tetramethylbutyl)-6-benzotriazolylphenol] comprising 2,2'-methylenebis[4-(1,1,3,3-tetramethylbutyl)-6-benzotriazolylphenol] type I crystal transformation which exhibits diffraction peaks at diffraction angles (2θ±0.1°) of 7.1°, 8.6°, 14.3°, 16.1°, 18.1° and 23.0° in powder X-ray diffraction analysis with Cu-Kα radiation, and the 2,2'-methylenebis[4-(1,3,3-tetramethylbutyl)-6-benzotriazolylphenol] type II crystal transformation as set forth in the above-mentioned 4) in an amount of 1% by weight or more based on the amount of the type I crystal transformation.

6) A sixth aspect of the present invention relates to a mixture of 2,2'-methylenebis[4-(1,1,3,3-tetramethylbutyl)-6-benzotriazolylphenol] comprising the crystalline 2,2'-methylenebis[4-(1,1,3,3-tetramethylbutyl)-6-benzotriaz- olylphenol] type I crystal transformation as set forth in the above-mentioned 1) or 2), and the 2,2'-methylenebis[4-(1,1,3,3-tetramethylbutyl)-6-benzotriazolylphenol] type II crystal transformation as set forth in the above-mentioned 4) in an amount of 1% by weight or more based on the amount of the type I crystal transformation.

7) A seventh aspect of the present invention relates to a method for preparing the 2,2'-methylenebis[4-(1,1,3,3-tetramethylbutyl)-6-benzotriazolylphenol] type II crystal transformation as set forth in the above-mentioned 4), characterized by melting 2,2'-methylenebis[4-(1,1,3,3-tetramethylbutyl)-6-benzotriazolylphenol] at a temperature of 195° C. or more, and cooling and solidifying.

8) An eighth aspect of the present invention relates to a method for preparing the mixture of 2,2'-methylenebis[4-(1,1,3,3-tetramethylbutyl)-6-benzotriazolylphenol] as set forth in the above-mentioned 5) or 6), characterized by melting 2,2'-methylenebis[4-(1,1,3,3-tetramethylbutyl)-6-benzotriazolylphenol] at a temperature of 195° C. or more, and cooling and solidifying.

9) A ninth aspect of the present invention relates to a UV light absorber characterized by containing the crystalline 2,2'-methylenebis[4-(1,1,3,3-tetramethylbutyl)-6-benzotriazolylphenol] type I crystal transformation as set forth in the above-mentioned 1) or 2).

10) A tenth aspect of the present invention relates to an emulsion composition characterized by containing the crystalline 2,2'-methylenebis[4-(1,1,3,3-tetramethylbutyl)-6-benzotriazolylphenol] type I crystal transformation as set forth in the above-mentioned 1) or 2).

11) An eleventh aspect of the present invention relates to a polymer material characterized by containing the crystalline 2,2'-methylenebis[4-(1,1,3,3-tetramethylbutyl)-6-benzotriazolylphenol] type I crystal transformation as set forth in the above-mentioned 1) or 2) or the emulsion composition as set forth in the above-mentioned 10).

12) A twelfth aspect of the present invention relates to a UV light absorber characterized by containing the 2,2'-methylenebis[4-(1,1,3,3-tetramethylbutyl)-6-benzotriazolylphenol] type II crystal transformation as set forth in the above-mentioned 4).

13) A thirteenth aspect of the present invention relates to an emulsion composition characterized by containing the 2,2'-methylenebis[4-(1,1,3,3-tetramethylbutyl)-6-benzotriazolylphenol] type II crystal transformation as set forth in the above-mentioned 4).

14) A fourteenth aspect of the present invention relates to a polymer material characterized by containing the 2,2'-methylenebis[4-(1,1,3,3-tetramethylbutyl)-6-benzotriazolylphenol] type II crystal transformation as set forth in the above-mentioned 4) or the emulsion composition as set forth in the above-mentioned 13).

15) A fifteenth aspect of the present invention relates to a UV light absorber characterized by containing the mixture of 2,2'-methylenebis[4-(1,1,3,3-tetramethylbutyl)-6-benzotriazolylphenol] as set forth in the above-mentioned 5) or 6).

16) A sixteenth aspect of the present invention relates to an emulsion composition characterized by containing the mixture of 2,2'-methylenebis[4-(1,1,3,3-tetramethylbutyl)-6-benzotriazolylphenol] as set forth in the above-mentioned 5) or 6).

17) A seventeenth aspect of the present invention relates to a polymer material characterized by containing the mixture of 2,2'-methylenebis[4-(1,1,3,3-tetramethylbutyl)-6-benzotriazolylphenol] as set forth in the above-mentioned 5) or 6) or the emulsion composition as set forth in the above-mentioned 16).

As mentioned above, 2,2'-methylenebis[4-(1,1,3,3-tetramethylbutyl)-6-benzotriazolylphenol] prepared by a known method is in a form of fine powder, and causes problems in workability and working environment such as scattering of dust during handling.

As a result of several investigations, the present inventors found that 2,2'-methylenebis[4-(1,1,3,3-tetramethylbutyl)-6-benzotriazolylphenol] type I crystal transformation prepared by the method according to the present invention has an excellent UV light absorptive power, exert little sublimation or volatilization, are easy to handle and excellent in workability at use, and cause little dust, and consequently reached a resolution of the problems.

In addition, the present inventors found that substances obtained by melting, cooling and solidifying 2,2'-methylenebis[4-(1,1,3,3-tetramethylbutyl)-6-benzotriazolylphenol] prepared by a known method or 2,2'-methylenebis[4-(1,1,3,3-tetramethylbutyl)-6-benzotriazolylphenol] type I crystal transformation according to the present invention also are in a state of solid causing little dust, and have an inherent ability as UV light absorber, in particular an excellent UV light absorptive power when they are used in a state where an emulsion composition therefrom is adsorbed on a fiber, and consequently reached a resolution of the problems.

In general, changes in physical properties for the same compound depending on crystallization condition seldom occur and do not arise in all compounds. Therefore, the above-mentioned changes in the present invention are a specific property for 2,2'-methylenebis[4-(1,1,3,3-tetramethylbutyl)-6-benzotriazolylphenol]. In addition, there exists no information on the crystal analysis of 2,2'-methylenebis[4-(1,1,3,3-tetramethylbutyl)-6-benzotriazolylphenol] until now. Thus, the results of the present invention can not be easily found.

Further, the present inventors conducted powder X-ray diffraction analysis with Cu-Kα radiation for 2,2'-methylenebis[4-(1,1,3,3-tetramethylbutyl)-6-benzotriazolylphenol] type I crystal transformation and type II crystal transformation in order to make the characteristics of these crystals clearer. As a result, it was found that the low dusting type I crystal transformation of the present invention has diffraction peaks at diffraction angles (2θ±0.1°) of 7.1°, 8.6°, 14.3°, 16.1°, 18.1° and 23.0° (see, FIG. 1), on the other hand the type II crystal transformation of the present invention is amorphous and does not exhibit a distinct diffraction peak but a halo (see, FIG. 2).

Hereinafter, the present invention will be explained in detail.

First of all, the present inventors obtained crystalline 2,2'-methylenebis[4-(1,1,3,3-tetramethylbutyl)-6-benzotriazolylphenol] type I crystal transformation causing little dust by crystallizing a reaction product of 4-(1,1,3,3-tetramethylbutyl)-6-benzotriazolylphenol of formula (2), dialkylamine, formaldehyde and a base in the presence of ketone.

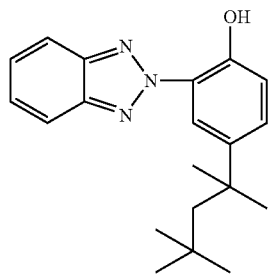

(2)

Next, the crystalline 2,2'-methylenebis[4-(1,1,3,3-tetramethylbutyl)-6-benzotriazolylphenol] type I crystal transformation obtained according to the above-mentioned procedure was subjected to powder X-ray diffraction analysis with Cu-Kα radiation. As a result, it was found that the type I crystal transformation is a substance with a good crystallizability and diffraction peaks at diffraction angles (2θ±0.1°) of 7.1°, 8.6°, 14.3°, 16.1°, 18.1° and 23.0° in the powder X-ray diffraction analysis (FIG. 1 is a powder X-ray diffraction pattern of the substance).

Further, the present inventors measured the compaction degree of the crystalline powder of 2,2'-methylenebis[4-(1,1,3,3-tetramethylbutyl)-6-benzotriazolylphenol] type I crystal transformation obtained according to the present invention with powder test. As a result, it was found that the crystalline powder has a compaction degree ranging from 28 to 35 on the average which is lower than that ranging from 45 to 48 in the conventional fine powder produced from the same compound by using xylene or the like and that the crystalline powder has a high flowability.

Generally, the compaction degree in powder test has been known as a factor most closely related to the flowability of powder, and it is said that the lower the measured value of a powder is, the higher the flowability thereof is, and that powders having a compaction degree of 40 or more have an undesirable flowability. From the fact, it is clear that the crystalline 2,2'-methylenebis[4-(1,1,3,3-tetramethylbutyl)-6-benzotriazolylphenol] type I crystal transformation of the present invention has more flowability than 2,2'-methylenebis[4-(1,1,3,3-tetramethylbutyl)-6-benzotriazolylphenol] prepared by using xylene or the like in the prior art.

The ketone solvents used in the crystallization of the low dusting 2,2'-methylenebis[4-(1,1,3,3-tetramethylbutyl)-6-benzotriazolylphenol] type I crystal transformation of the present invention include acetone, methyl ethyl ketone, methyl isobutyl ketone and the like, and they may be used alone or as a mixed solvent. Further, the solvents may be used as a mixed solvent with alcohols such as methanol, isopropyl alcohol, n-butanol, cyclohaxanol, ethylene glycol or propylene glycol, water, ethers such as dioxane, dibutyl ether, ethylisoamyl ether or ethylphenyl ether; hydrocarbons such as n-decane, 3-ethylhexane, methylcyclohexane, toluene, ethylbenzene, cumene, o-cymene, p-cymene, m-cymene, o-xylene, m-xylene, p-xylene, t-butylbenzene, 1-butyl-4-methylbenzene, 1-butyl-2-methylbenzene, 1,2,3-trimethylbenzene, 1,2,4-trimethylbenzene, 1,3,5-trimethylbenzene or 1,2,4,5-tetramethylbenzene; carboxylates such as butyl acetate or ethyl propionate; organic halides such as carbon tetrachloride, chlorobenzene or o-dichlorobenzene; nitrogen-containing compounds such as dimethylformamide, dimethylacetamide, quinoline, n-butylamine or 2-methyl pyrrolidone. They can be used under not only a normal pressure but also a reduced pressure or a pressure.

The condition under which the solvent is used is not specifically limited, but it is natural that the yield is greatly influenced by the solubility.

Further, the present inventors conducted several investigation on the type II crystal transformation of the present invention, and found that the type II crystal transformation can be prepared as a solid with little dust by melting 2,2'-methylenebis[4-(1,1,3,3-tetramethylbutyl)-6-benzotriazolylphenol] obtained by a known method or the low dusting type I crystal transformation of the present invention at a temperature of 195° C. or more and then cooling and solidifying, and that the solid can be easily obtained also as a substance in a flake form by using a flaker or the like. In the meantime, depending on the condition of heating process, the above-mentioned type I crystal transformation may be obtained in addition to the type II crystal transformation. For example, in a case where the heating process is conducted at about 200° C., a mixture of the type I crystal transformation and the type II crystal transformation can be prepared. In the mixture, the type II crystal transformation is contained in an amount of 1% by weight or more, and the mixture can be also obtained in a solid form with little dust.

Powder X-ray diffraction analysis may not show apparent difference in diffraction pattern between the mixture of the type I crystal transformation and type II crystal transformation in a mixing proportion prepared according to the present invention and 100% type I crystal transformation. However, the mixing proportion of the type I crystal transformation and the type II crystal transformation can be clarified by conducting a measurement with differential scanning calorimeter (TA Instrument Type 2920 DSC, sample amount of 1.3 mg, atmosphere in the oven of nitrogen flow with 50 ml/min., and heating rate at 10.0° C./min., hereinafter referred to as DSC).

In the DSC measurements, 100% type I crystal transformation shows an endothermic peak at around 200° C. due to melting and 100% type II crystal transformation shows an exothermic peak at around 130° C. (due to transition from type II to type I) and an endothermic peak at around 200° C. (due to melting of type I after the transition). Therefore, the mixing proportion of type II and type I based on the DSC measurements is determined by using a calibration curve prepared from calorimetric ratio of the exothermic peak of type II and the endothermic peak of type I which are measured with respective pure crystal transformation.

That is, the present invention can provide an amorphous type II crystal transformation which do not exhibit a distinct diffraction peak but a halo in powder X-ray diffraction with Cu-Kα radiation, and a mixture of type II and type I, in both a solid form with little dust by melting 2,2'-methylenebis [4-(1,1,3,3-tetramethylbutyl)-6-benzotriazolylphenol] or the 2,2'-methylenebis[4-(1,1,3,3-tetramethylbutyl)-6-benzotriazolylphenol] type I crystal transformation of the present invention with no solvent or a solvent at a normal pressure or under a reduced pressure or a pressure at a temperature of 195° C. or more, preferably a temperature ranging from 200° C. to 250° C. and then cooling. In addition, a substance in a flake form can be easily obtained by using a flaker or the like.

The solvent which may be present in the preparation of the 2,2'-methylenebis[4-(1,1,3,3-tetramethylbutyl)-6-benzotriazolylphenol] type II crystal transformation of the present invention includes water, and alcohols such as n-butanol, cyclohaxanol, ethylene glycol or propylene glycol, ethers such as dioxane, dibutyl ether, ethylisoamyl ether or ethylphenyl ether; hydrocarbons such as n-decane, 3-ethylhexane, methylcyclohexane, toluene, ethylbenzene, cumene, o-cymene, p-cymene, m-cymene, o-xylene, m-xylene, p-xylene, t-butylbenzene, 1-butyl-4-methylbenzene, 1-butyl-2-methylbenzene, 1,2,3-trimethylbenzene, 1,2,4-trimethylbenzene, 1,3,5-trimethylbenzene or 1,2,4,5-tetramethylbenzene; carboxylates such as butyl acetate or ethyl propionate; ketones such as methyl ethyl ketone or methyl isobutyl ketone; organic halides such as carbon tetrachloride, chlorobenzene or o-dichlorobenzene; nitrogen-containing compounds such as dimethylformamide, dimethylacetamide, quinoline, n-butylamine or 2-methyl pyrrolidone, and the solvent may be used alone or as a mixed solvent.

The low dusting 2,2'-methylenebis[4-(1,1,3,3-tetramethylbutyl)-6-benzotriazolylphenol] type I crystal transformation and type II crystal transformation of the present invention can be mixed into polymer materials as UV light absorber in the usual way in a powder form, a flake form, a suspension or an emulsion composition. The polymer materials include resin compositions, fibers, rubber, paper and the like, and particularly an emulsion composition effective for dyeing is often used for fibers. Examples of the resin compositions are phenol resins, melamine resins, epoxy resins, polyurethane, polyimide, vinyl chloride, polyvinylacetal, polyethylene, polypropylene, polybutylene, polymethylpentene, polystyrene, polybutadiene resins, ethylene-propylene copolymers, ethylene-vinyl acetate copolymers, ethylene-methyl (ethyl) acrylate copolymers, polyester, acrylonitrile-styrene resins (AS), acrylonitrile-butadiene-styrene resins (ABS), polyethylene terephthalate (PET), polybutylene terephthalate, polycarbonate (PC), PC.ABS alloy, PC.PET alloy, polyphenylene ether resins, polyphenylene sulfide resins, methacrylate resins, polyamide resins, diallyl phthalate resins, silicone resins, unsaturated polyester or the like, and they can be used as polymer material with excellent weatherability for automobile related parts, OA equipment, electronic parts, household appliance, machine parts, building parts, medical accessory parts, household miscellaneous goods and the like.

The low dusting 2,2'-methylenebis[4-(1,1,3,3-tetramethylbutyl)-6-benzotriazolylphenol] type I crystal transformation and type II crystal transformation, and the mixture of type I crystal transformation and type II crystal transformation of the present invention can be added to a resin and so forth alone to exert an effective UV light absorptive power thereby making possible to prevent deterioration in quality, or can be also used in combination with antioxidants or light stabilizers that are known in the prior art, or can be mixed with hygroscopic agents, mildew-proofing agents, antifoaming agents or the like.

The emulsion composition containing the low dusting 2,2'-methylenebis[4-(1,1,3,3-tetramethylbutyl)-6-benzotriazolylphenol] type I crystal transformation or type II crystal transformation, or the mixture of type I crystal transformation and type II crystal transformation according to the present invention can prepared by emulsifying the low dusting 2,2'-methylenebis[4-(1,1,3,3-tetramethylbutyl)-6-benzotriazolylphenol] type I crystal transformation or type II crystal transformation, or the mixture of type I crystal transformation and type II crystal transformation optionally with additives of common use in the presence of emulsifying agents with the use of a machine for emulsifying and dispersing, such as a homogenizer, a colloid mill or a bead mill. Various surfactants can be used as the emulsifying agent without any limitation, and hygroscopic agents, mildew-proofing agents, antifoaming agents, antioxidants, light stabilizers or the like may be mixed as the additives of common use.

Concrete examples of the emulsifying agent that can be used in the present invention are anionic surfactants such as sodium stearate, sodium lauryl sulfate, sodium lauryl ether sulfate, sodium dodecyl benzene sulfonate or di-2-ethylhexyl sodium sulfosuccinate; cationic surfactants such as alkyltrimethyl ammonium chloride or triethanolamine monostearate formate; amphoteric surfactants such as sodium laurylaminopropionate; and non-ionic surfactants such as polyethylene glycol lauric acid monoester, polyethylene glycol lauric acid diester, polyoxyethylene stearate, diethylene glycol monooleyl ether or glycerin lauric acid monoester, and they can be alone or in a mixture thereof.

The hygroscopic agent which can be mixed into the emulsion composition or polymer material of the present invention includes for example propylene glycol, ethylene glycol, d-sorbitol or urea.

The mildew-proofing agent which can be mixed into the emulsion composition or polymer material of the present invention includes for example p-hydroxy benzoic acid or chloroacetamide.

The antifoaming agent which can be mixed into the emulsion composition or polymer material of the present invention includes for example silicones such as silicone resin, or organic polar compounds such as 2-ethylhexanol or polypropylene glycol.

The antioxidants which can be mixed into the emulsion composition or polymer material of the present invention includes for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-dinonyl-4-methylphenol, 2,6-di-tert-butyl-4-methoxymethylphenol, 2,4-dimethyl-6-(1'-methyl-undeca-1'-yl)phenol, 2,4-dimethyl-6-(1'-methyl-trideca-1'-yl)phenol and a mixture thereof; 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol and a mixture thereof; 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenylstearate, bis(3,5-di-tert-butyl-4-hydroxyphenyl)adipate and a mixture thereof; 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate or the like and 2,2'-methylene bis(6-tert-butyl-4-methylphenol), 2,2'-methylene bis(6-tert-butyl-4-ethylphenol), 2,2'-ethylidene bis(4,6-di-tert-butylphenol), 2,2'-ethylidene bis(6-tert-butyl-4-isobutylphenol), 4,4'-methylene bis(2,6-di-tert-butylphenol), 4,4'-methylene bis(6-tert-butyl-2-methylphenol), 1,1-bis(5-tert-butyl-4-hydroxy-2-methylphenyl)butane, ethylene glycol bis[3,3'-bis(3'-tert-butyl-4'-hydroxyphenyl)butyrate] or the like, and 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol or the like.

The light stabilizers which can be mixed into the emulsion composition or polymer material of the present invention includes for example benzotriazoles such as 2-(2'-hydroxy-5'-methylphenyl)benzotriazole, 2-(3',5'-di-tert-butyl-2-hydroxyphenyl)benzotriazole, 2-(5'-tert-butyl-2'-hydroxyphenyl)benzotriazole, 2-[2'-hydroxy-5'-(1,1,3,3-tetramethylbutyl)phenyl] benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(2'-hydroxy-4'-octoxyphenyl)benzotriazole, 2-(3',5'-di-tert-amyl-2'-hydroxyphenyl)benzotriazole or 2-[3'-tert-butyl-2'-hydroxy-5'-(n-octyloxycarbonylethyl)phenyl]-5-chlorobenzotriazole; benzophenones such as 4-hydroxy-, 4-methoxy-, 4-octoxy-, 4-decyloxy-, 4-dodecyloxy-, 4-benzyloxy-, 4,2',4'-trihydroxy-, 2'-hydroxy-4,4'-dimethoxy- or 4-(2-ethylhexyloxy)-2-hydroxy benzophenone; salicylates such as 4-tert-butylphenyl salicylate, phenyl salicylate or octylphenyl salicylate; resorcinols such as dibenzoyl resorcinol, bis(4-tert-butylbenzoyl resorcinol) or 2,4-di-tert-butylphenyl resorcinol; benzoates such as 3,5-di-tert-butyl-4-hydroxybenzoate or hexadecyl-3,5-di-tert-butyl-4-hydroxybenzoate; acrylates such as ethyl α-cyano-β,β-diphenyl acrylate or isooctyl α-cyano-β,β-diphenylacrylate; cinamates such as methyl α-carbomethoxy cinnamate or methyl α-cyano-β,β-methyl-p-methoxy cinnamate; acid esters such as bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate or bis(1,2,2,6,6-pentamethyl-4-piperidyl)adipate; oxanilides such as 4,4'-dioctyloxyoxanilide, 2,2-diethoxyoxyxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxanilide or 2-ethoxy-5-tert-butyl-2'-ethoxyoxanilide; triazines such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-dodecyloxyphenyl)-4,6-bis(2,4-dimethylphenyl)-1,3,5-triazine.

BEST MODE FOR CARRYING OUT THE INVENTION

Hereinafter, the present invention is described based on examples to which the present invention is not limited at all.

I. Preparation and evaluation of low dusting 2,2'-methylenebis[4-(1,1,3,3-tetramethylbutyl)-6-benzotriazolylphenol] type I crystal transformation

Condition and Method for Measurement

Powder X-ray diffraction analysis with Cu-Kα radiation was conducted with TFD-18kw manufactured by Mac Science Co., Ltd. under the condition of anti-cathode Cu-Kα (1.5405 Å), 40 kV-50 mA and a scanning rate at 2.000°/min. In addition, a diffraction angle (2θ) in powder X-ray diffraction analysis for the same crystal form is identical with an error of about ±0.1°, and therefore clearly indicates a difference in crystal transformation. The relative intensity of a diffraction radiation may effect change in the intensity ratio depending on the particle diameter of the sample to be measured.

Powder test was conducted with Hosokawa Micron Powder Tester TYPE-E and a 100 cc cylinder container with a diameter of 5 cm was used for determination of an apparent specific gravity.

The measurement of loose apparent specific gravity was conducted by gently filling the container to an overflowing point with the powder, weighing the powder after leveling off any extra powder above the container surface, and determining the loose specific gravity by dividing the weight (g) of the powder by 100.

The measurement of dense apparent specific gravity was conducted by filling the container with the powder in a similar manner as in the loose apparent specific gravity, tapping 180 times, then weighing the powder after leveling off any extra powder above the container surface, and determining the dense apparent specific gravity by dividing the weight (g) of the powder by 100. In addition, compaction degree was calculated according to the equation below:

$$\text{Compaction degree} = 100(P-A)/P$$

wherein A is a loose apparent specific gravity and P is a dense apparent specific gravity.

EXAMPLE 1

Figure 1:
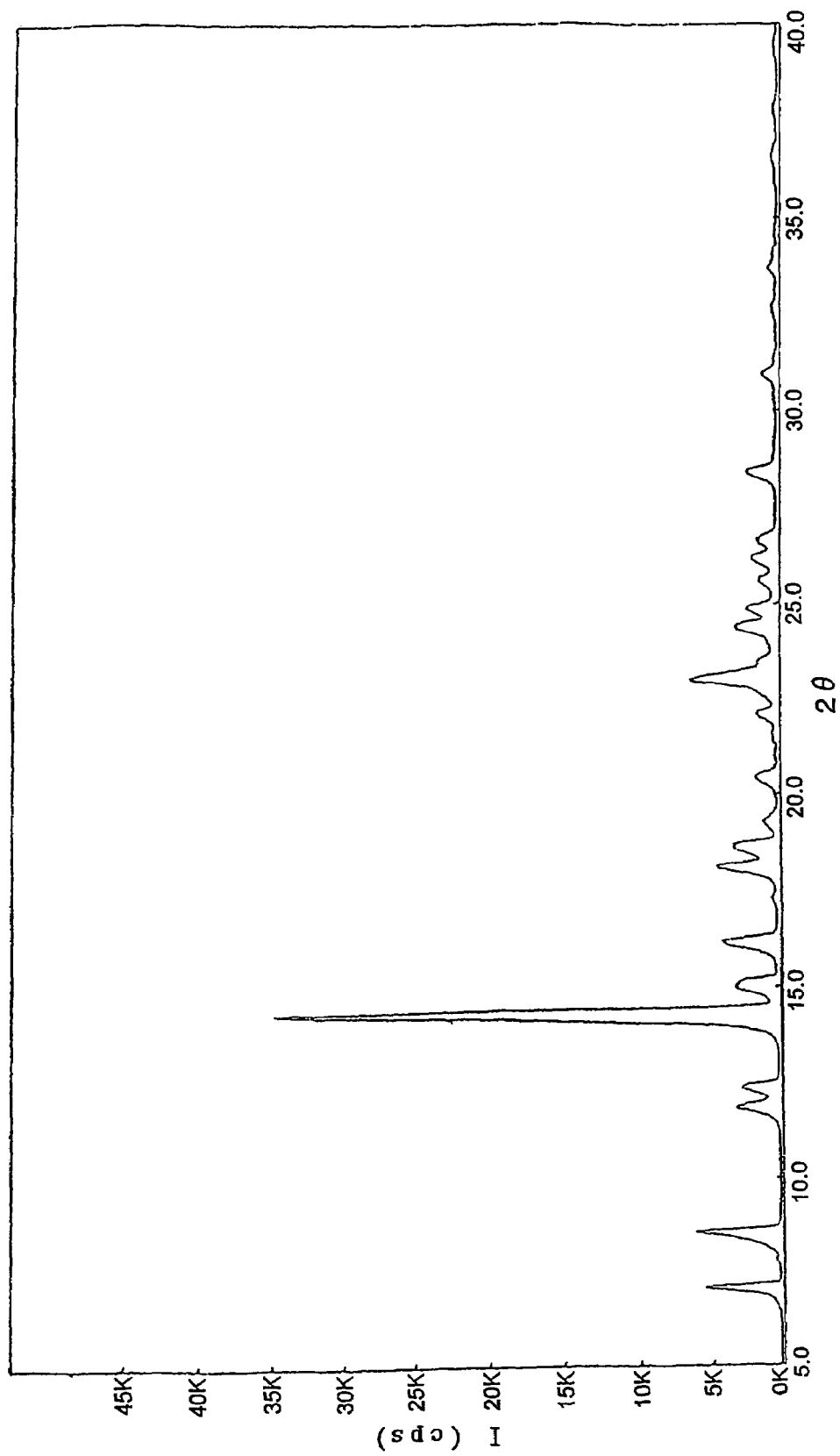
FIG. 1 shows an X-ray diffraction pattern for the low dusting crystalline 2,2'-methylenebis[4-(1,1,3,3-tetramethylbutyl)-6-benzotriazolylphenol] type I crystal transformation prepared in Example 1 according to the present invention.

Preparation of low dusting 2,2'-methylenebis[4-(1,1,3,3-tetramethylbutyl)-6-benzotriazolylphenol] type I crystal transformation To a container with a stirrer, 634 g of 4-(1,1,3,3-tetramethylbutyl)-6-benzotriazolyl phenol, 52 g of paraformaldehyde, 110 g of diethylamine and 600 ml of xylene were charged, and reacted at a temperature of 95 to 100° C. for 24 hours. Then, 31 g of 28% sodium methylate solution in methanol was added and reacted at a temperature of 145 to 150° C. for 10 hours. Upon completion of the reaction, the reaction solution was washed with water, 100 ml of methyl isobutyl ketone was added to the xylene layer and crystallized. The resulting crystal was filtered to obtain 594.0 g (yield 92%) of 2,2'-methylenebis[4-(1,1,3,3-tetramethylbutyl)-6-benzotriazolylphenol] as white crystal (causing no dust) with a melting point of 199 to 200° C. The resulting compound had a mass of 659 (calculated value 658.9) in mass spectrometry. In addition, powder X-ray diffraction analysis with Cu-Kα radiation indicated that the resulting crystal was a crystal material having distinct diffraction peaks at diffraction angles (2θ±0.1°) of 7.1°, 8.6°, 14.3°, 16.1°, 18.1° and 23.0° as shown in FIG. 1.

Further, the compaction degree of the resulting crystal was 30 in powder test.

COMPARATIVE EXAMPLE 1

Preparation of 2,2'-methylenebis[4-(1,1,3,3-tetramethylbutyl)-6-benzotriazolylphenol] according to conventional process To a container with a stirrer, 634 g of 4-(1,1,3,3-tetramethylbutyl)-6-benzotriazolyl phenol, 52 g of paraformaldehyde, 110 g of diethylamine and 600 ml of xylene were charged, and reacted at a temperature of 95 to 100° C. for 24 hours. Then, 31 g of 28% sodium methylate solution in methanol was added and reacted at a temperature of 145 to 150° C. for 10 hours. Upon completion of the reaction, the reaction solution was washed with water, xylene was distilled off and crystallized from methanol to obtain 581.1 g (yield 90%) of 2,2'-methylenebis[4-(1,1,3,3-tetramethylbutyl)-6-benzotriazolylphenol] as white crystal (causing dust) with a melting point of 199 to 200° C. The resulting compound had a mass of 659 (calculated value 658.9) in mass spectrometry. In addition, the compaction degree of the resulting crystal was 48 in powder test, and suggested that the powder had a low flowability.

EXAMPLE 2

Light Stabilization Effect for Polymer Material 100 parts by weight of polyethylene powder or polypropylene powder was thoroughly mixed in a mixer with 0.05, 0.2 or 0.5 part by weight of the compound prepared in Example 1 (dusts were not discharged upon mixing) and the mixture was thereafter subjected to melt extrusion through an extruder with a cylinder temperature of 200° C. and a diameter of 25 mm to form pellets. The pellets were subjected to compression molding into a shape of sheet at 210° C. to form test pieces having a thickness of 0.25 mm. Dumbbell specimens for tensile test were punched out of the test pieces. Specimens without light stabilizers for comparative examples were prepared in a similar manner as above and subjected to measurement.

These specimens were irradiated in WEL-75XS-HS-BEC type Xenon Sunshine Long-Life Weather-O-Meter manufactured by Suga Test Instrument Co., Ltd. at a black panel temperature of 80° C. and lowering in tensile strength of each specimen with time was compared. The tensile test was conducted at a temperature of 23±2° C., a relative humidity of 50±5% and a test rate of 50±5.0 mm/min. with DSS-5000 type tension tester manufactured by Shimadzu Corporation. Tension strength was determined according to the equation below:

$$Ts = S/T \cdot W$$

wherein Ts=tension strength (kgf/mm$^2$),
T=thickness of a sample (mm),
W=width of a sample (mm), and
S=maximum strength of a sample (kgf).

The results are summarized in Table 1.

As clear from the results shown in Table 1, the low dusting 2,2'-methylenebis[4-(1,1,3,3-tetramethylbutyl)-6- benzotriazolylphenol] type I crystal transformation according to the present invention shows excellent stabilization effect (that is, prolongation of time to deterioration).

TABLE 1

| Resin | Amount of light stabilizer added (% by weight) | 200 hrs. | 400 hrs. | 600 hrs. | 800 hrs. | 1000 hrs. | 1200 hrs. |
|---|---|---|---|---|---|---|---|
| Polypropylene | None | 3.14 | 2.12 | 0 | — | — | — |
| | 0.05 | 4.04 | 3.13 | 2.99 | — | — | — |
| | 0.2 | 4.24 | 3.94 | 3.89 | — | — | — |
| | 0.5 | 4.46 | 4.35 | 4.14 | — | — | — |
| Polyethylene | None | 2.41 | 2.25 | 2.24 | 2.10 | 1.89 | 0 |
| | 0.05 | 3.36 | 3.26 | 3.14 | 3.07 | 3.03 | 2.84 |
| | 0.2 | 3.94 | 3.76 | 3.54 | 3.48 | 3.42 | 3.22 |
| | 0.5 | 4.46 | 4.26 | 4.12 | 3.92 | 3.80 | 3.72 |

II. Preparation and evaluation of low dusting 2,2'-methylenebis[4-(1,1,3,3-tetramethylbutyl)-6-benzotriazolylphenol] type II crystal transformation and mixture of type I crystal transformation and type II crystal transformation Condition and Method for Measurement A mixing proportion of type II and type I was determined based on DSC measurements by using a calibration curve prepared from calorimetric ratio of the exothermic peak of type II and the endothermic peak of type I which were measured with respective pure crystal transformation.

The DSC measurements were conducted with TA Instrument Type 2920 DSC under the condition of a sample amount of 1.3 mg, atmosphere in the oven of nitrogen flow with 50 ml/min., and a heating rate at 10.0° C./min.

In a similar manner as the above-mentioned I, powder X-ray diffraction analysis with Cu-Kα radiation was conducted with TFD-18kw manufactured by Mac Science Co., Ltd. under the condition of anti-cathode Cu-Kα (1.5405 Å), 40 kV-50 mA and a scanning rate at 2.000°/min. In addition, a diffraction angle (2θ) in powder X-ray diffraction analysis for the same crystal form is identical with an error of about ±0.1°, and therefore clearly indicates a difference in crystal transformation. The relative intensity of a diffraction radiation may effect change in the intensity ratio depending on the particle diameter of the sample to be measured.

UV light absorbers were evaluated by subjecting a sample prepared by treating a dyed polyester fabric with a UV light absorber (an emulsion composition) to an exposure test for 300 hours and determining discoloration or fading of the sample.

In the exposure test, Table Sun TS-1 manufactured by Suga Test Instrument Co., Ltd. was used.

COMPARATIVE EXAMPLE 2

Figure 4:
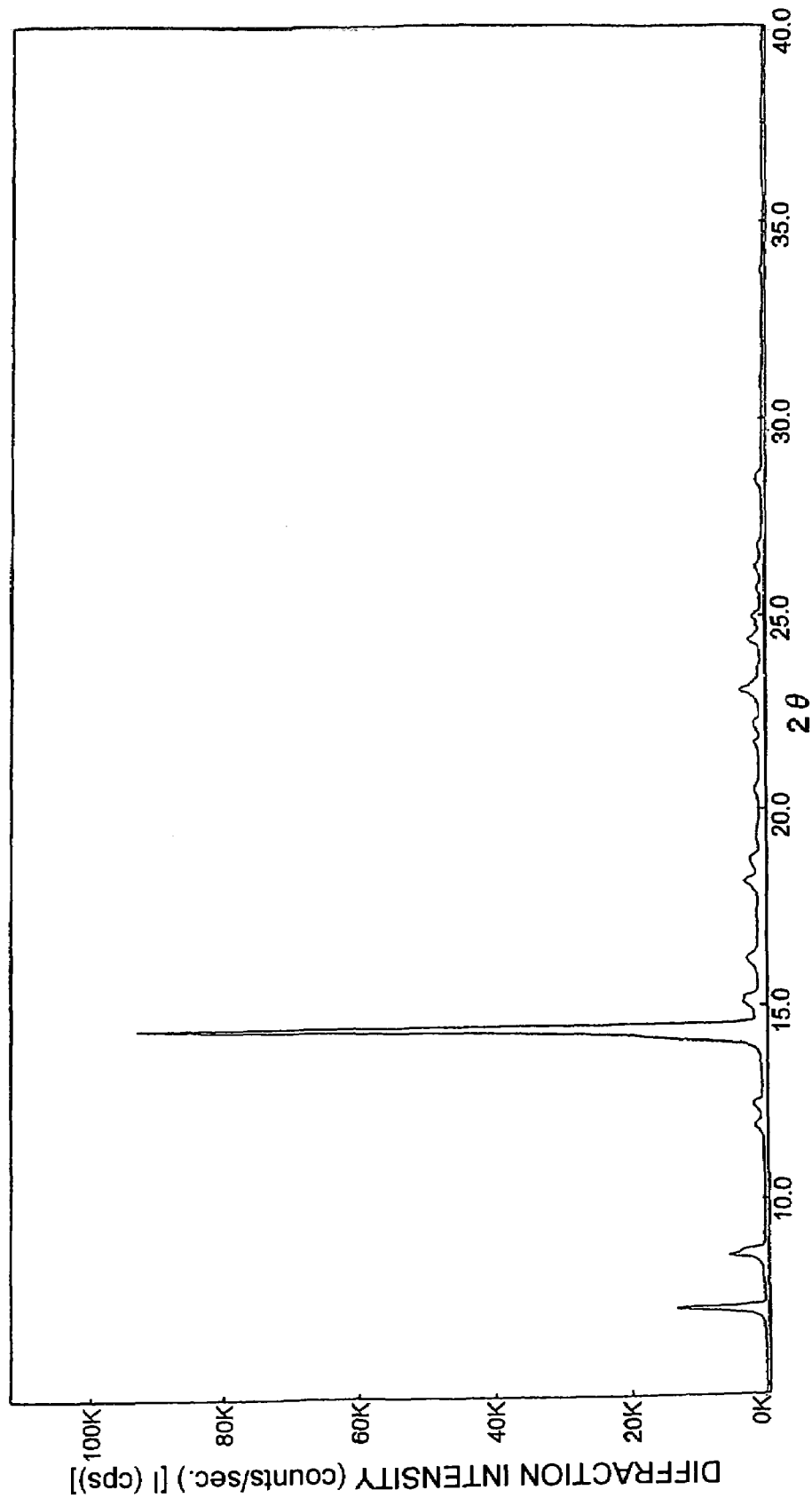
FIG. 4 shows an X-ray diffraction pattern for the compound prepared in Comparative Example 2 according to a conventional process.
Figure 5:
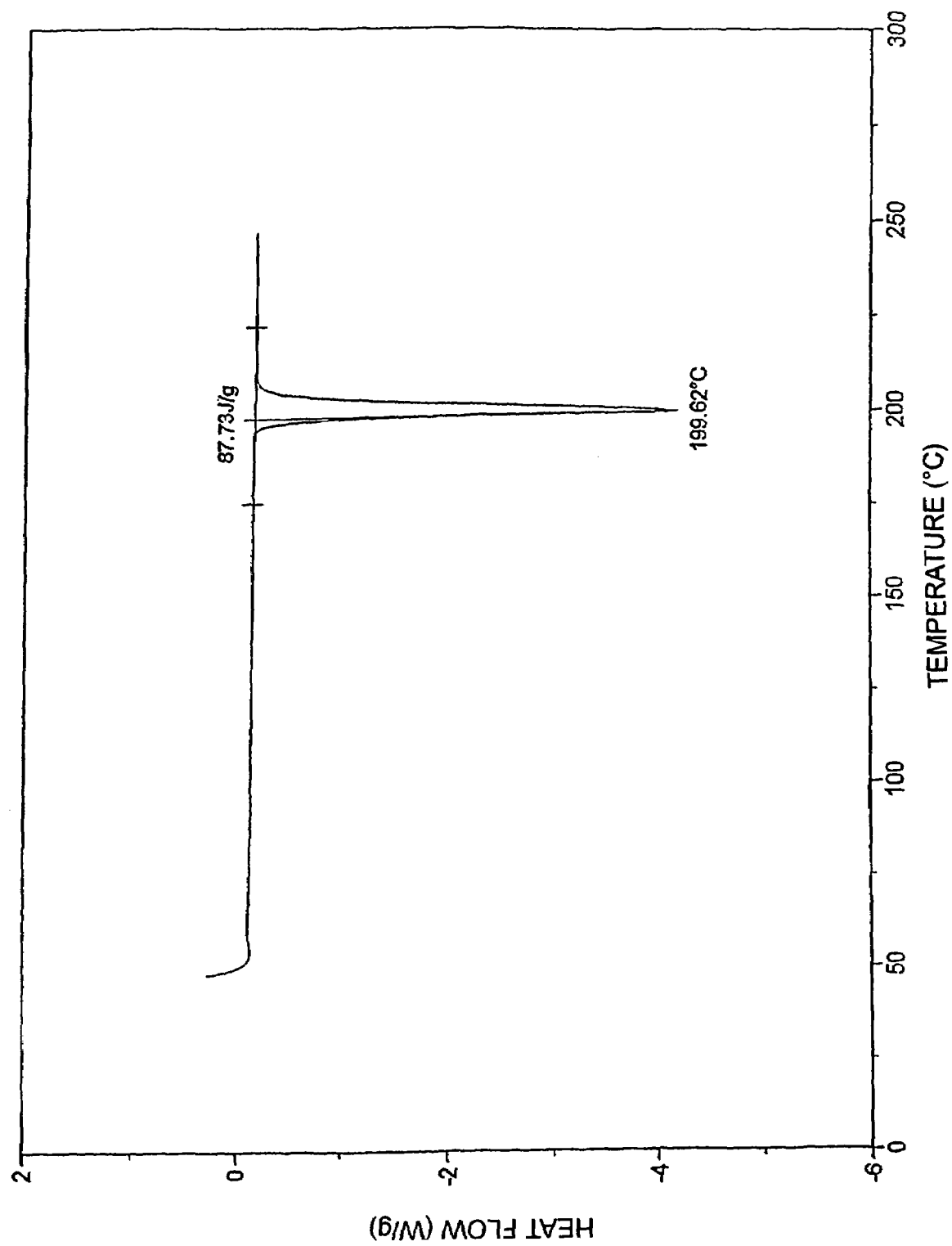
FIG. 5 shows a DSC chart for the compound prepared in Comparative Example 2 according to a conventional process.

Preparation of 2,2'-methylenebis[4-(1,1,3,3-tetramethylbutyl)-6-benzotriazolylphenol] according to conventional process To a container with a stirrer, 63.4 kg of 4-(1,1,3,3-tetramethylbutyl)-6-benzotriazolyl phenol, 5.2 kg of paraformaldehyde, 11.0 kg of diethylamine and 60 L of xylene were charged, and reacted at a temperature of 95 to 100° C. for 24 hours. Then, 3.1 kg of 28% sodium methylate solution in methanol was added and reacted under nitrogen gas at temperature of 145 to 150° C. for 10 hours. The reaction solution was washed with water, and crystallized by cooling the xylene layer to 10° C. The resulting crystal was filtered to obtain 56.8 kg (yield 88%) of 2,2'-methylenebis[4-(1,1,3,3-tetramethylbutyl)-6-benzotriazolylphenol] as white solid in a shape of fine powder (causing dust). Powder X-ray diffraction analysis for the resulting crystal with Cu-Kα radiation indicated that it was type I having distinct diffraction peaks at diffraction angles (2θ±0.1°) of 7.1°, 8.6°, 14.3°, 16.1°, 18.1° and 23.0° as shown in FIG. 4. Further, DSC analysis indicated that the crystal was 100% type I as shown in FIG. 5.

EXAMPLE 3

Figure 2:
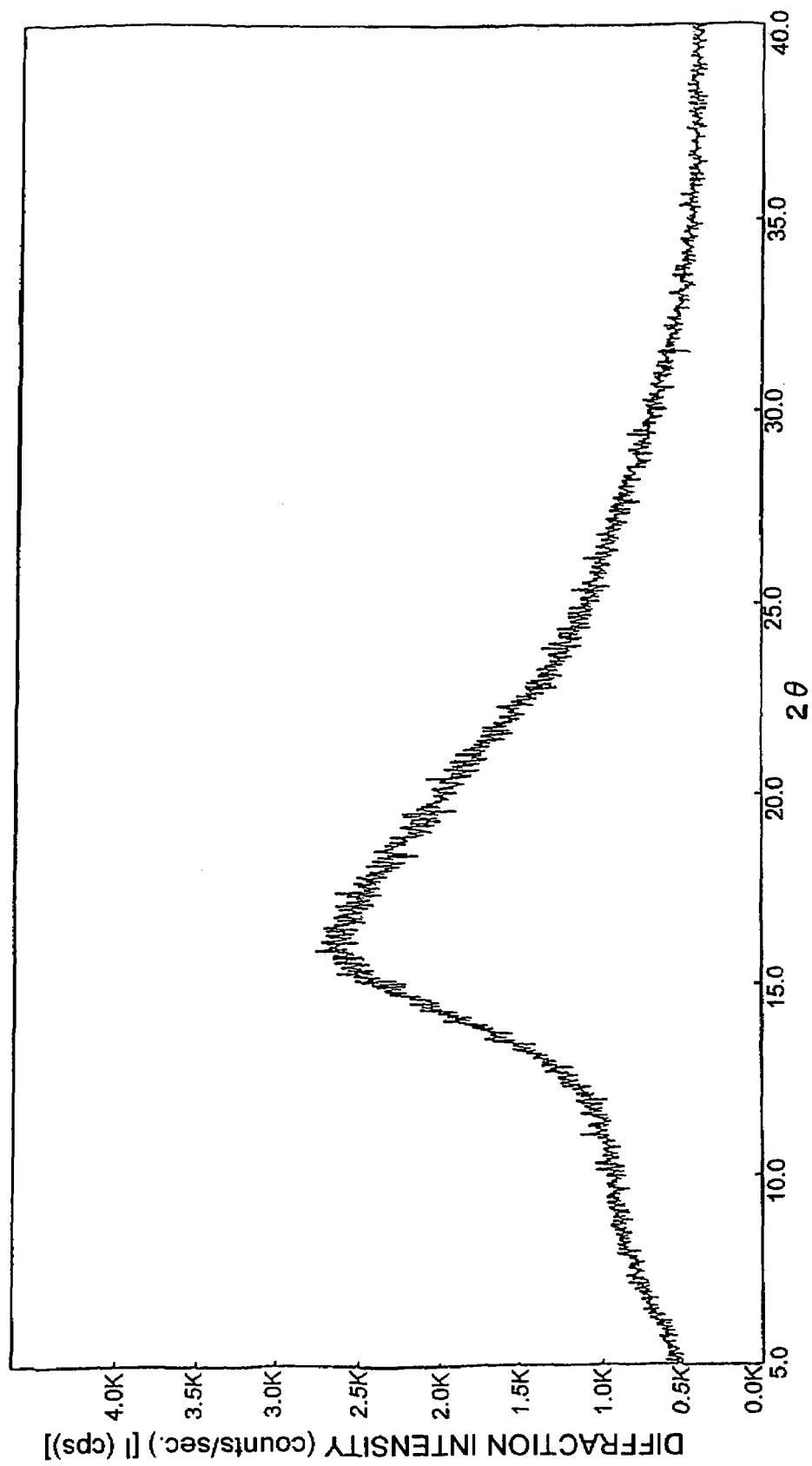
FIG. 2 shows an X-ray diffraction pattern for the amorphous 2,2'-methylenebis[4-(1,1,3,3-tetramethylbutyl)-6-benzotriazolylphenol] which is a novel type II crystal transformation prepared in Example 3 according to the present invention.
Figure 3:
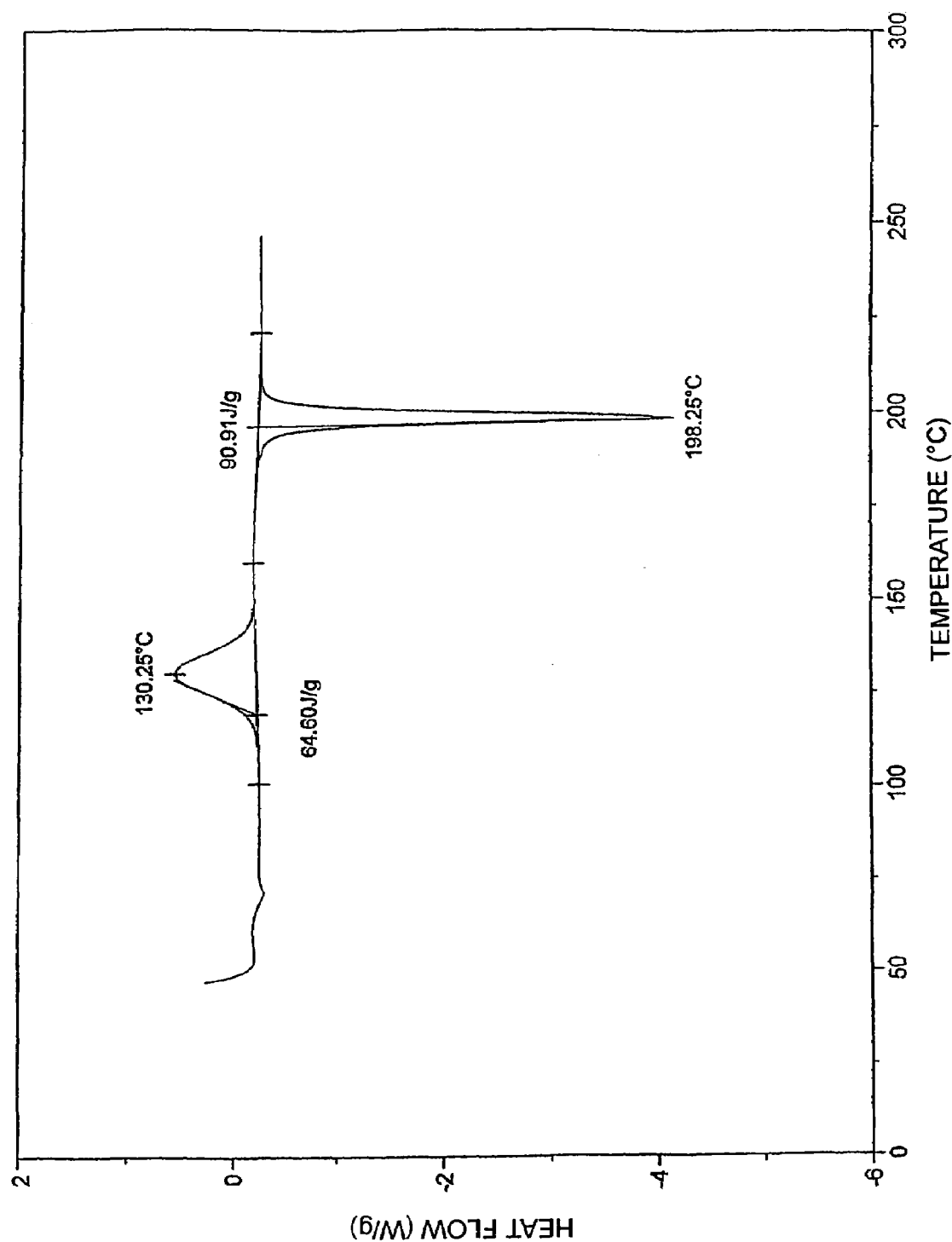
FIG. 3 shows a DSC chart for the novel type II crystal transformation prepared in Example 3 according to the present invention.

Preparation low dusting 2,2'-methylenebis[4-(1,1,3,3-tetramethylbutyl)-6-benzotriazolylphenol] type II crystal transformation 2,2'-methylenebis[4-(1,1,3,3-tetramethylbutyl)-6-benzotriazolylphenol] obtained in Comparative Example 2 was melted at a temperature of 220 to 240° C. and cooled to 10° C. with a flaker to obtain crystal in a shape of flake (causing no dust). Powder X-ray diffraction analysis for the crystal obtained by grinding the resulting flake with Cu-Kα radiation indicated that it was type II which was amorphous and which did not exhibit distinct diffraction peak but a halo as shown in FIG. 2. In the meantime, the powder X-ray diffraction analysis indicated that the crystal from Example 3 was 100% type II. Further, DSC analysis for 100% type II crystal transformation from Example 3 exhibited one exothermic peak at 130.2° C. and one endothermic peak at 198.2° C. as shown in FIG. 3.

EXAMPLE 4

Figure 6:
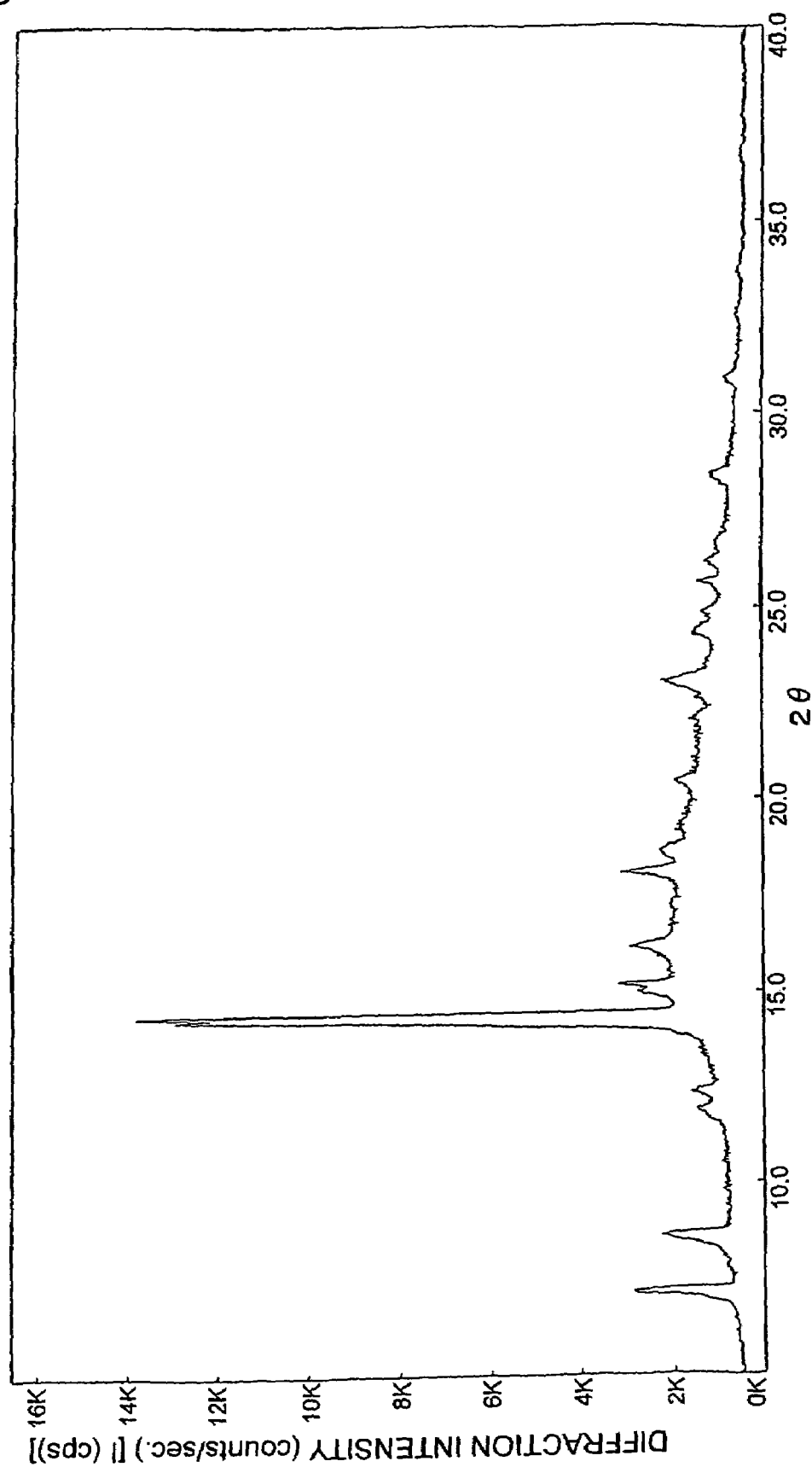
FIG. 6 shows an X-ray diffraction pattern for the mixture of type I crystal transformation and type II crystal transformation prepared in Example 4 according to the present invention.
Figure 7:
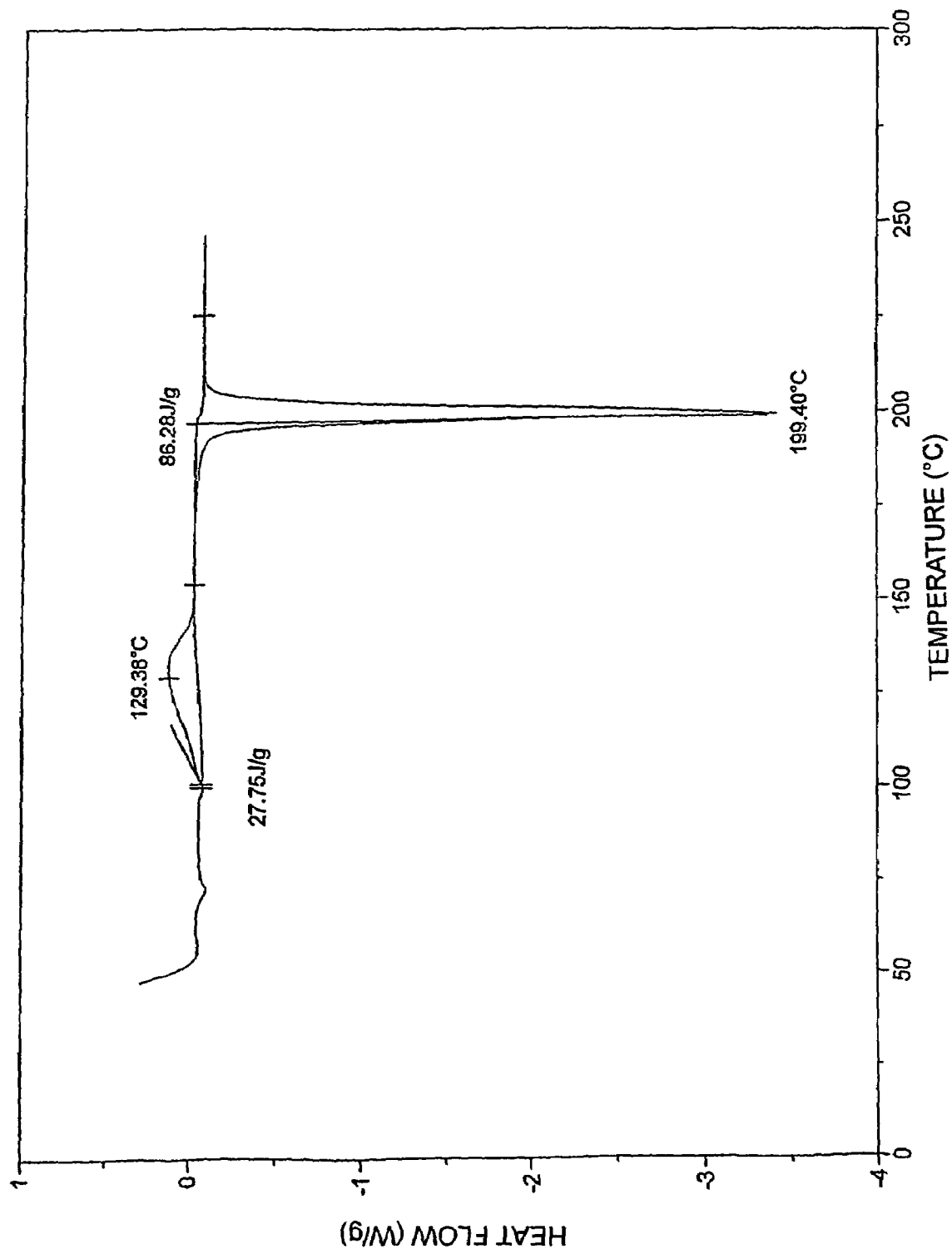
FIG. 7 shows a DSC chart for the mixture of type I crystal transformation and type II crystal transformation prepared in Example 4 according to the present invention.

Preparation of low dusting mixture of 2,2'-methylenebis[4-(1,1,3,3-tetramethylbutyl)-6-benzotriazolylphenol] type I crystal transformation and type II crystal transformation 2,2'-methylenebis[4-(1,1,3,3-tetramethylbutyl)-6-benzotriazolylphenol] obtained in a similar manner as Comparative Example 2 was melted at a temperature of 205 to 210° C. and cooled to 10° C. with a flaker to obtain crystal in a shape of flake (causing no dust). Powder X-ray diffraction analysis for the crystal obtained by grinding the resulting flake with Cu-Kα radiation indicated that it was type I having distinct diffraction peaks at diffraction angles (2θ±0.1°) of 7.1°, 8.6°, 14.3°, 16.1°, 18.1° and 23.0° as shown in FIG. 6. Further, from DSC analysis result [a calorimetric ratio of endothermic peak of type I to exothermic peak of type II was 75.7 (type I):24.3 (type II)] as shown in FIG. 7, the mixing proportion of type I crystal transformation and type II crystal transformation in the resulting flake was 51.0% by weight of type I and 49.0% by weight of type II.

EXAMPLE 5

Figure 8:
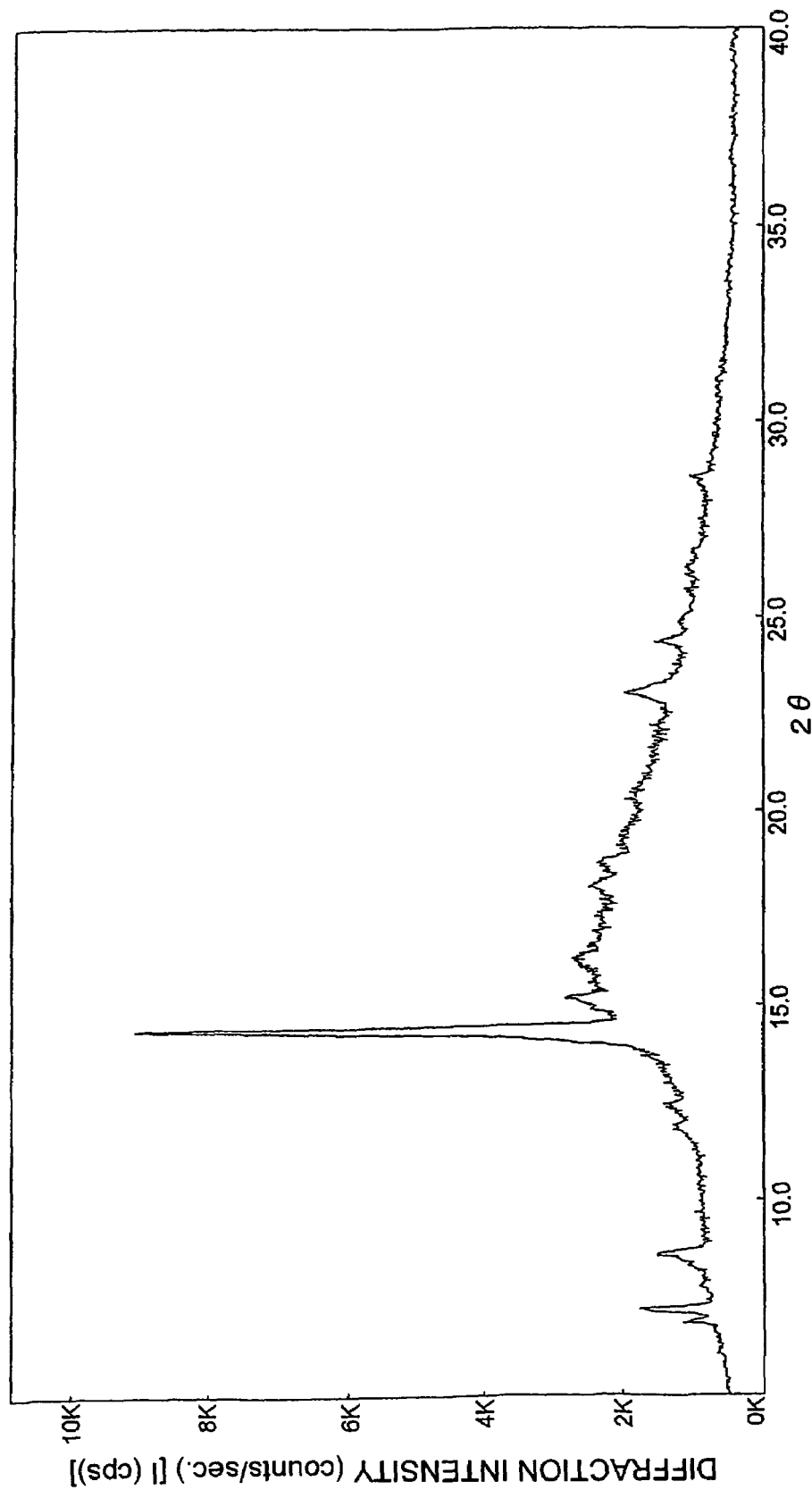
FIG. 8 shows an X-ray diffraction pattern for the mixture of type I crystal transformation and type II crystal transformation prepared in Example 5 according to the present invention.

Preparation of low dusting mixture of 2,2'-methylenebis[4-(1,1,3,3-tetramethylbutyl)-6-benzotriazolylphenol] type I crystal transformation and type II crystal transformation 2,2'-methylenebis[4-(1,1,3,3-tetramethylbutyl)-6-benzotriazolylphenol] obtained in a similar manner as Comparative Example 2 was melted at a temperature of 210 to 215° C. and cooled to 10° C. with a flaker to obtain crystal in a shape of flake (causing no dust). Powder X-ray diffraction analysis for the crystal obtained by grinding the resulting flake with Cu-Kα radiation indicated that it was type I having distinct diffraction peaks at diffraction angles (2θ±0.1°) of 7.1°, 8.6°, 14.3°, 16.1°, 18.1° and 23.0° as shown in FIG. 8. Further, from DSC analysis result [a calorimetric ratio of endothermic peak of type I to exothermic peak of type II was 64.9 (type I):35.1 (type II)], the mixing proportion of type I crystal transformation and type II crystal transformation in the resulting flake was 16.9% by weight of type I and 83.1% by weight of type II.

EXAMPLE 6

Preparation of low dusting mixture of 2,2'-methylenebis[4-(1,1,3,3-tetramethylbutyl)-6-benzotriazolylphenol] type I crystal transformation and type II crystal transformation 2,2'-methylenebis[4-(1,1,3,3-tetramethylbutyl)-6-benzotriazolylphenol] obtained in a similar manner as Comparative Example 2 was melted at a temperature of 195 to 200° C. and cooled to 10° C. with a flaker to obtain crystal in a shape of flake (causing no dust). Powder X-ray diffraction analysis for the crystal obtained by grinding the resulting flake with Cu-Kα radiation indicated that it was type I having distinct diffraction peaks at diffraction angles (2θ±0.1°) of 7.1°, 8.6°, 14.3°, 16.1°, 18.1° and 23.0°. Further, from DSC analysis result [a calorimetric ratio of endothermic peak of type I to exothermic peak of type II was 93.9 (type I):6.1 (type II)], the mixing proportion of type I crystal transformation and type II crystal transformation in the resulting flake was 90.0% by weight of type I and 10.0% by weight of type II.

FORMULATION EXAMPLE 1

Preparation of Emulsion Composition

Emulsion composition A was prepared by adding 25.0 parts by weight of 2,2'-methylenebis[4-(1,1,3,3-tetramethylbutyl)-6-benzotriazolylphenol] obtained in Example 3, 7.5 parts by weight of sodium dodecylbenzenesulfonate, 2.0 parts by weight of glycerin lauric acid monoester, 1.0 part by weight of sodium laurylaminopropionate, 12.7 parts by weight of propylene glycol and 0.2 part by weight of chloroacetamide into 51.6 parts by weight of water under stirring with a bead mill. Similarly, emulsion compositions B, C and D were prepared by adding 2,2'-methylenebis[4-(1,1,3,3-tetramethylbutyl)-6-benzotriazolylphenol] obtained in Example 4, 2,2'-methylenebis[4-(1,1,3,3-tetramethylbutyl)-6-benzotriazolylphenol] obtained in Comparative Example 2 according to a conventional process, and no 2,2'-methylenebis[4-(1,1,3,3-tetramethylbutyl)-6-benzotriazolylphenol], respectively, in place of 2,2'-methylenebis[4-(1,1,3,3-tetramethylbutyl)-6-benzotriazolylphenol] obtained in Example 3.

FORMULATION EXAMPLE 2

Preparation of Evaluation Sample

Evaluation sample A was prepared by dipping a polyester fabric dyed with Kayalon Polyester Yellow BRL-S200 (trade name, manufactured by Nippon Kayaku Co., Ltd.), Kayalon Polyester Navy Blue EX-SF200 (trade name, manufactured by Nippon Kayaku Co., Ltd.) and Kayalon Polyester Light Scarlet G-S200 (trade name, manufactured by Nippon Kayaku Co., Ltd.) in emulsion composition A prepared in Formulation Example 1, washing with water and drying. Similarly, evaluation samples B, C and D were prepared by using emulsion compositions B, C and D, respectively, in place of emulsion composition A.

EXAMPLE 7

Measurement of Resistance to Discoloration

Evaluation samples prepared in Formulation Example 2 were subjected to an exposure test (Table Sun TS-1 manufactured by Suga Test Instruments Co., Ltd.) and level of discoloration and fading after UV light irradiation of 300 hours was examined by visually comparing color shade between a sample before irradiation and the sample after irradiation. Fastness to light was evaluated as follows: no change (level 4), very tiny change (level 3), a little change (level 2) and apparent fading (level 1) wherein the more the level is, the higher the fastness to light is. The result are shown in Table 2.

TABLE 2

| Evaluation sample | 2,2'-methylenebis[4-(1,1,3,3-tetramethylbutyl)-6-benzotriazolyl phenol] added in emulsion composition | Level of fastness to light |
| --- | --- | --- |
| A | 100% type II product obtained in Example 3 | 4 |
| B | 49% type II product obtained in Example 4 | 4 |
| C | 100% type I product obtained in Comparative Example 2 | 3 |
| D | None | 1 |

EXAMPLE 8

Figure 9:
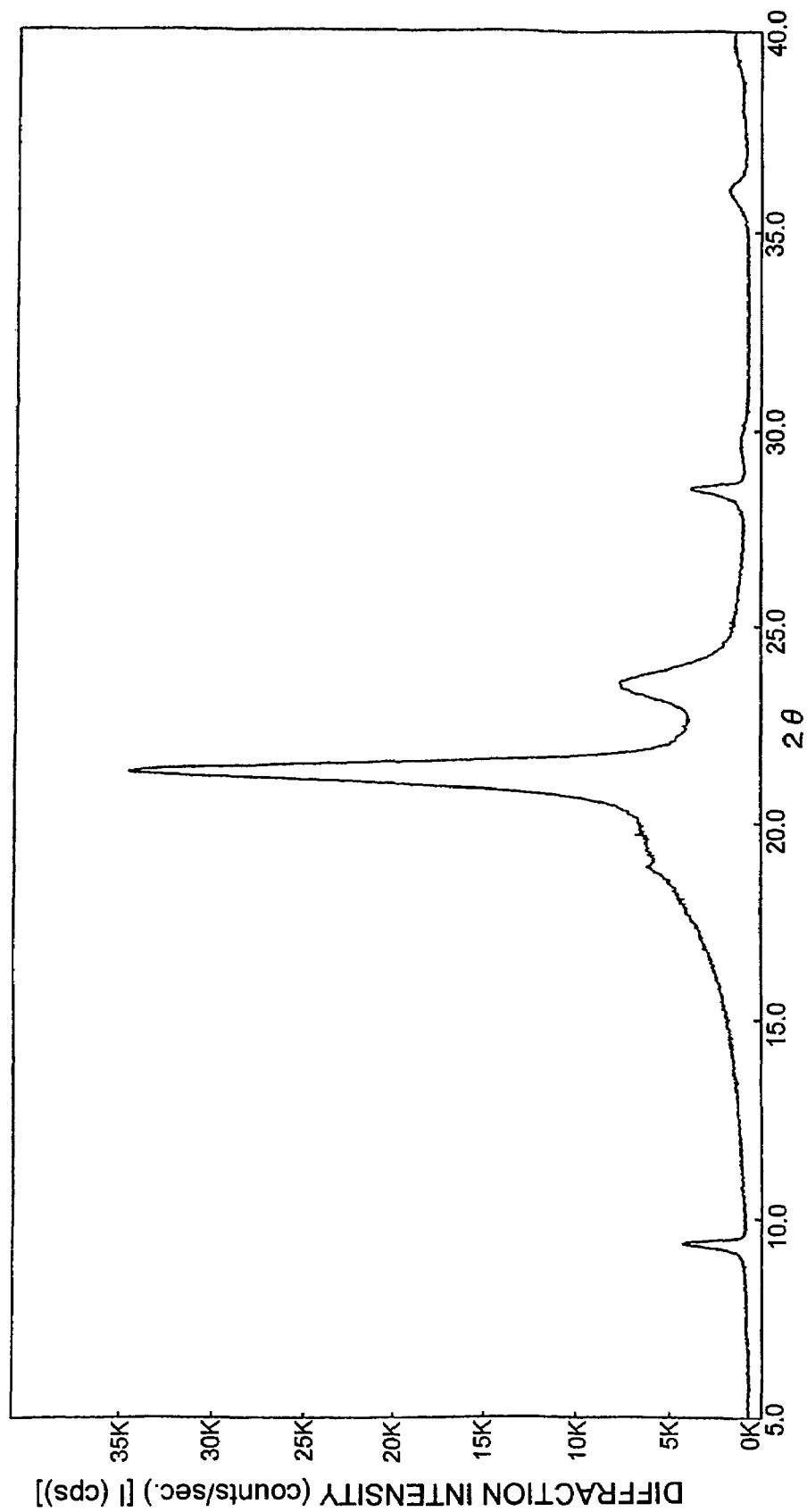
FIG. 9 shows an X-ray diffraction pattern for a sheet made by using the compound prepared in Example 3 (100% type II) as light stabilizer.
Figure 10:
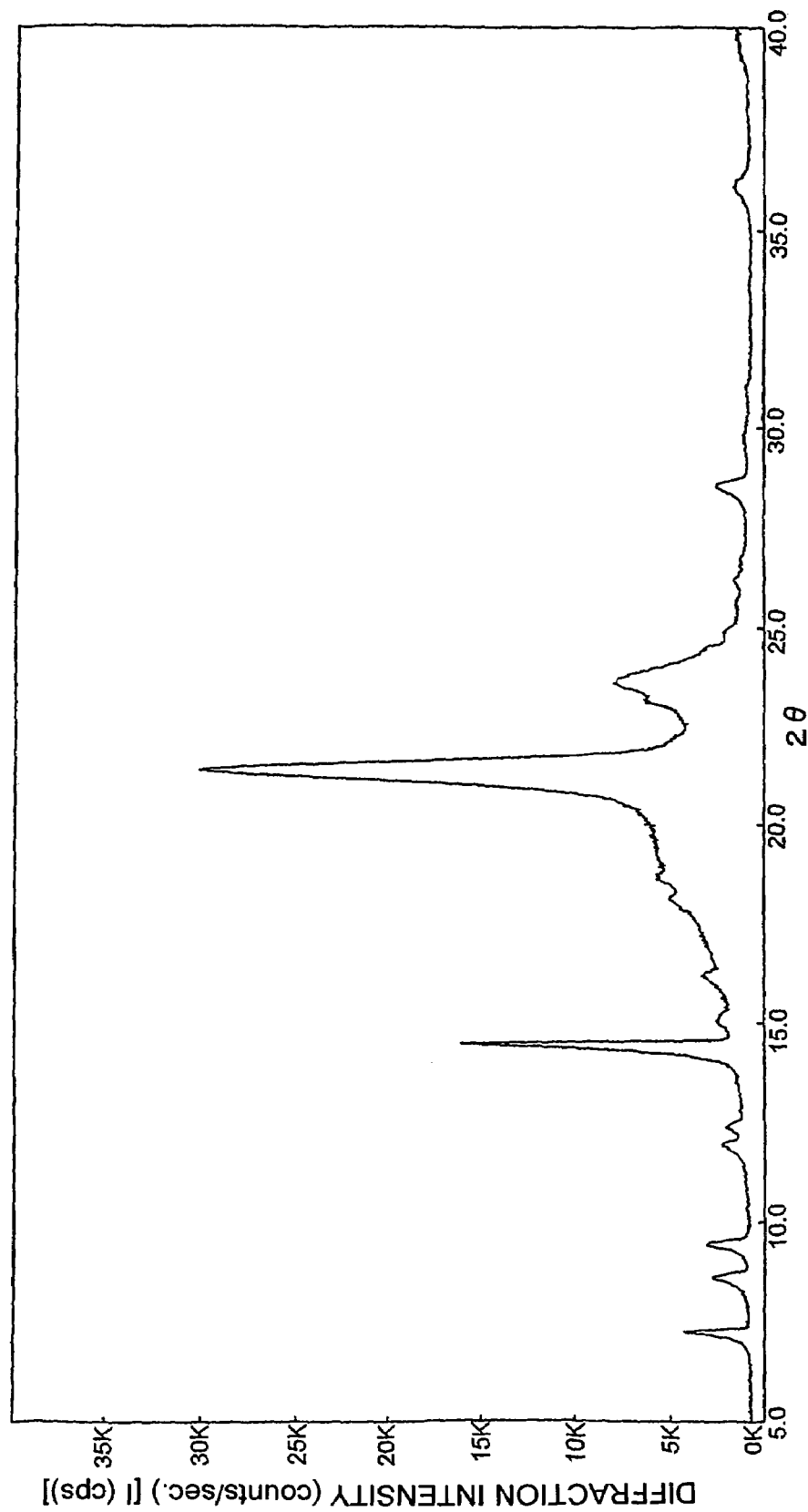
FIG. 10 shows an X-ray diffraction pattern for a sheet made by using the compound prepared in Comparative Example 2 (100% type I according to a conventional process) as light stabilizer.

Measurement of Light Stabilization Effect for Polymer Material 100 parts by weight of polyethylene powder was thoroughly mixed in a mixer with 2.0 parts by weight of the compound prepared in Example 3 (100% type II) and the mixture was thereafter subjected to melt extrusion through an extruder with a cylinder temperature of 180° C. and a diameter of 25 mm to form pellets. The pellets were subjected to compression molding into a shape of sheet having a thickness of 0.25 mm at 180° C. Dumbbell specimens for tensile test were punched out of the sheets. Further, specimens containing the compound prepared in Comparative Example 2 (100% type I) or no light stabilizer were prepared as control for comparison in a similar manner as above and subjected to measurement of light stabilization effect. Further, X-ray diffraction analysis for these specimens indicated that the sheet prepared by using the compound prepared in Example 3 (100% type II) as light stabilizer exhibited no diffraction peak of the light stabilizer as shown in FIG. 9 and indicated the same diffraction pattern as that of a sheet containing no light stabilizer. On the contrary, the diffraction pattern of the sheet produced by adding the compound prepared in Comparative Example 2 (100% type I according to a conventional process) is shown in FIG. 10, and exhibits diffraction peaks at diffraction angles (2θ±0.1°) of 7.1°, 8.6°, 14.3°, 16.1°, 18.1° and 23.0° which are characteristics of the compound prepared in Comparative Example 2 (100% type I according to a conventional process).

These specimens were irradiated in Xenon Sunshine Long-Life Weather-O-Meter at a black panel temperature of 80° C. and lowering in tensile strength of each specimen with time was compared. The tensile test was conducted at a temperature of 23±2° C., a relative humidity of 50±5% and a test rate of 50±5.0 mm/min. Tension strength was determined according to the equation below:

$$Ts=S/T \cdot W$$

wherein Ts=tension strength (kgf/mm$^2$),
T=thickness of a sample (mm),
W=width of a sample (mm), and
S=maximum strength of a sample (kgf).
The results are summarized in Table 3.

TABLE 3

| | (Unit: kgf) | | | |
|---|---|---|---|---|
| Light stabilizer | 0 hr. | 400 hrs. | 800 hrs. | 1200 hrs. |
| Example 3 (100% type II) | 4.69 | 4.51 | 3.95 | 3.77 |
| Comparative Example (100% type I according to conventional process) | 4.35 | 4.10 | 3.21 | 2.23 |
| None | 4.65 | 2.41 | 1.80 | 0 |

As clear from the results shown in Table 3, 2,2'-methylenebis[4-(1,1,3,3-tetramethylbutyl)-6-benzotriazolylphenol] type II crystal transformation according to the present invention shows more excellent stabilization effect (that is, prolongation of time to deterioration) than the type I crystal transformation according to the conventional process.

As mentioned above, 2,2'-methylenebis[4-(1,1,3,3-tetramethylbutyl)-6-benzotriazolylphenol] type I crystal transformation and II crystal transformation, and a crystal transformation mixture comprising the type II crystal transformation in an amount of 1% by weight or more based on the amount of the type I crystal transformation, which are prepared according to the present invention, cause little dust and are UV light absorbers effective for working environment.

What is claimed is:

1. A low dusting crystalline 2,2'-methylenebis[4-(1,1,3,3-tetramethylbutyl)-6-benzotriazolylphenol] type I crystal transformation of formula (1)

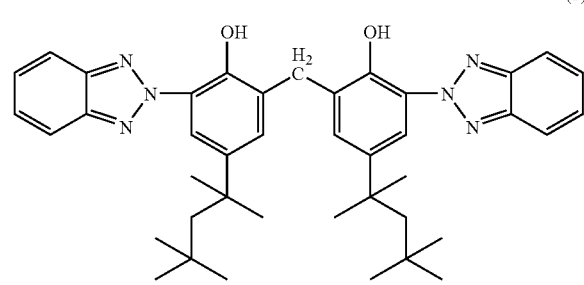

(1)

which exhibits diffraction peaks at diffraction angles (2θ+0.1°) of 7.1°, 8.6°, 14.3°, 16.1°, 18.1° and 23.0° in powder X-ray diffraction analysis with Cu-Kα radiation, which has a compaction degree of 35 or less in powder test.

2. 2,2'-methylenebis[4-(1,1,3,3-tetramethylbutyl)-6-benzotriazolylphenol] type II crystal transformation of formula (1)

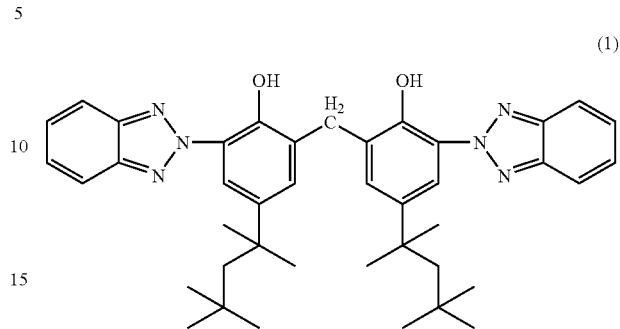

(1)

characterized in that it does not exhibit a distinct diffraction peak but a halo in powder X-ray diffraction analysis with Cu-Kα radiation and that is amorphous.

3. A mixture of 2,2'-methylenebis[4-(1,1,3,3-tetramethylbutyl)-6-benzotriazolylphenol] comprising 2,2'-methylenebis[4-(1,1,3,3-tetramethylbutyl)-6-benzotriazolylphenol] type I crystal transformation which exhibits diffraction peaks at diffraction angles (2θ+0.1°) of 7.1°, 8.6°, 14.3°, 16.1°, 18.1° and 23.0° in powder X-ray diffraction analysis with Cu-Kα radiation, and the 2,2'-methylenebis[4-(1,1,3,3-tetramethylbutyl)-6-benzotriazolylphenol] type II crystal transformation according to claim 2 in an amount of 1% by weight or more based on the amount of the type I crystal transformation.

4. A mixture of 2,2'-methylenebis[4-(1,1,3,3-tetramethylbutyl)-6-benzotriazolylphenol] comprising:
the crystalline 2,2'-methylenebis[4-(1,1,3,3-tetramethylbutyl)-6-benzotriazolylphenol] type I crystal transformation according to claim 1,
and the 2,2'-methylenebis[4-(1,1,3,3-tetramethylbutyl)-6-benzotriazolylphenol] type II crystal transformation of formula (1)

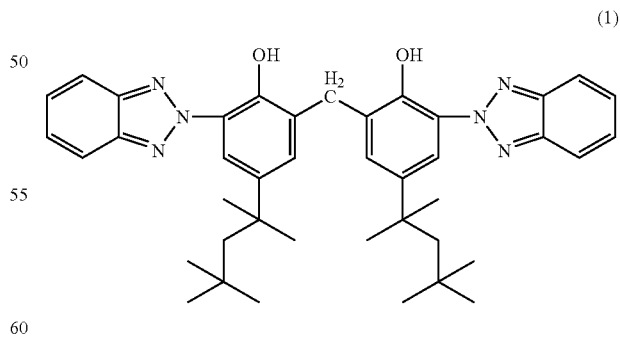

(1)

characterized in that it does not exhibit a distinct diffraction peak but a halo in powder X-ray diffraction analysis with Cu-Kα radiation and that is amorphous, in an amount of 1% by weight or more based on the amount of the type I crystal transformation.

5. A method for preparing the 2,2'-methylenebis[4-(1,1,3,3-tetramethylbutyl)-6-benzotriazolylphenol] type II crystal transformation according to claim 2, characterized by melting 2,2'-methylenebis[4-(1,1,3,3-tetramethylbutyl)-6-benzotriazolylphenol] at a temperature of 195° C. or more, and cooling and solidifying.

6. A method for preparing the mixture of 2,2'-methylenebis[4-(1,1,3,3-tetramethylbutyl)-6-benzotriazolylphenol] according to claim 3, characterized by melting 2,2'-methylenebis[4-(1,1,3,3-tetramethylbutyl)-6-benzotriazolylphenol] at a temperature of 195° C. or more, and cooling and solidifying.

7. A UV light absorber characterized by containing the crystalline 2,2'-methylenebis[4-(1,1,3,3-tetramethylbutyl)-6-benzotriazolylphenol] type I crystal transformation according to claim 1.

8. An emulsion composition characterized by containing the crystalline 2,2'-methylenebis[4-(1,1,3,3-tetramethylbutyl)-6-benzotriazolylphenol] type I crystal transformation according to claim 1.

9. A polymer material characterized by containing the crystalline 2,2'-methylenebis[4-(1,1,3,3-tetramethylbutyl)-6-benzotriazolylphenol] type I crystal transformation according to claim 1 or an emulsion composition containing the crystalline 2,2'-methylenebis[4-(1,1,3,3-tetramethylbutyl)-6-benzotriazolylphenol] type I crystal transformation.

10. A UV light absorber characterized by containing the 2,2'-methylenebis[4-(1,1,3,3-tetramethylbutyl)-6-benzotriazolylphenol] type II crystal transformation according to claim 2.

11. An emulsion composition characterized by containing the 2,2'-methylenebis[4-(1,1,3,3-tetramethylbutyl)-6-benzotriazolylphenol] type II crystal transformation according to claim 2.

12. A polymer material characterized by containing the 2,2'-methylenebis[4-(1,1,3,3-tetramethylbutyl)-6-benzotriazolylphenol] type II crystal transformation according to claim 2 or an emulsion composition containing the 2,2'-methylenebis[4-(1,1,3,3-tetramethylbutyl)-6-benzotriazolylphenol] type II crystal transformation.

13. A UV light absorber characterized by containing the mixture of 2,2'-methylenebis[4-(1,1,3,3-tetramethylbutyl)-6-benzotriazolylphenol] according to claim 3.

14. An emulsion composition characterized by containing the mixture of 2,2'-methylenebis[4-(1,1,3,3-tetramethylbutyl)-6-benzotriazolylphenol] according to claim 3.

15. A polymer material characterized by containing the mixture of 2,2'-methylenebis[4-(1,1,3,3-tetramethylbutyl)-6-benzotriazolylphenol] according to claim 3 or an emulsion composition containing the mixture of 2,2'-methylenebis[4-(1,1,3,3-tetramethylbutyl)-6-benzotriazolylphenol].

16. A low dusting crystalline 2,2'-methylenebis[4-(1,1,3,3-tetramethylbutyl)-6-benzotriazolylphenol] type I crystal transformation of formula (1)

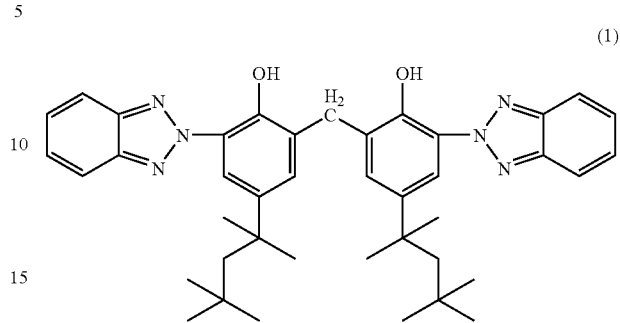

(1)

which exhibits diffraction peaks at diffractions angles (2θ±0.1°) of 7.1°, 8.6°, 14.3°, 16.1°, 18.1° and 23.0° in powder X-ray diffraction analysis with Cu-Kα radiation, produced by crystallizing 2,2'-methylenebis[4-(1,1,3,3-tetramethylbutyl)-6-benzotriazolylphenol] in the presence of an aromatic hydrocarbon solvent and a polar solvent.

17. A method of preparing a low dusting crystalline 2,2'-methylenebis[4-(1,1,3,3-tetramethylbutyl)-6-benzotriazolylphenol] type I crystal transformation of formula (1)

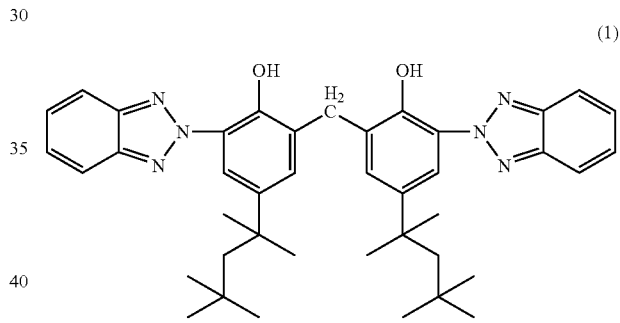

(1)

which exhibits diffractions peaks at diffractions angles (2θ±0.1°) of 7.1°, 8.6°, 14.3°, 16.1°, 18.1° and 23.0° in powder X-ray diffraction analysis with Cu-Kα radiation, characterized by crystallizing 2,2'-methylenebis[4-(1,1,3,3-tetramethylbutyl)-6-benzotriazolylphenol] in the presence of an aromatic hydrocarbon solvent and a polar solvent.

18. A method for preparing crystalline 2,2'-methylenebis[4-(1,1,3,3-tetramethylbutyl)-6-benzotriazolylphenol] type I crystal transformation according to claim 1, characterized by crystallizing 2,2'-methylenebis[4-(1,1,3,3-tetramethylbutyl)-6-benzotriazolylphenol] in the presence of ketone.

* * * * *

UNITED STATES PATENT AND TRADEMARK OFFICE
CERTIFICATE OF CORRECTION

PATENT NO.         : 7,326,744 B2                                            Page 1 of 1
APPLICATION NO. : 10/493575
DATED              : February 5, 2008
INVENTOR(S)        : Naohiko Fukuoka et al.

It is certified that error appears in the above-identified patent and that said Letters Patent is hereby corrected as shown below:

Title Page item 73

(73) Assignee, change "Chempiro Kaei Kaisha, Limited" to -- Chemipro Kasei Kaisha, Limited --.

Signed and Sealed this

Second Day of September, 2008

JON W. DUDAS
*Director of the United States Patent and Trademark Office*